(12) United States Patent
Jaynes et al.

(10) Patent No.: US 11,690,894 B2
(45) Date of Patent: *Jul. 4, 2023

(54) TRANSGENIC CORN WITH ANTIFUNGAL PEPTIDE AGM182 (DN:0113.18)

(71) Applicants: Genvor Inc., Dallas, TX (US); The United States of America, as represented by the Secretary of Agriculture, Washington, DC (US)

(72) Inventors: Jesse M. Jaynes, Auburn, AL (US); Kanniah Rajasekaran, Metairie, LA (US); Jeffrey W. Cary, Covington, LA (US); Ronald Sayler, Farmington, AR (US); Rajtilak Majumdar, Metairie, LA (US)

(73) Assignees: GENVOR INC., Dallas, TX (US); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 72 days.

This patent is subject to a terminal disclaimer.

(21) Appl. No.: 17/352,445

(22) Filed: Jun. 21, 2021

(65) Prior Publication Data
US 2021/0308219 A1 Oct. 7, 2021

Related U.S. Application Data

(63) Continuation of application No. 16/134,336, filed on Sep. 18, 2018, now Pat. No. 11,083,775.

(51) Int. Cl.
*C12N 15/82* (2006.01)
*C07K 14/435* (2006.01)
*A61K 38/17* (2006.01)

(52) U.S. Cl.
CPC ...... *A61K 38/1767* (2013.01); *C12N 15/8205* (2013.01); *C12N 15/8216* (2013.01); *C12N 15/8282* (2013.01)

(58) Field of Classification Search
None
See application file for complete search history.

(56) References Cited

U.S. PATENT DOCUMENTS 5,294,442 A 3/1994 Cotty
11,083,775 B2 * 8/2021 Jaynes ............ C07K 14/43509

OTHER PUBLICATIONS

Chen et al, 2015, World Mycotoxin Journal, 8:211-224.*
Rajasekaran et al, 2018, Plant Science, 270:150-156.*
Shigenaga et al, 1990, The Journal of Biological Chemistry, 265:21350-21354.*
Anonymous "The Value of Proactive Mycotoxin Prevention in the Age of the Food Safety Modernization Act—a White Paper" , in, Vicam, Waters Corporation, 2017, pp. 8.
Bedre, et al. "Genome-wide transcriptome analysis of cotton *Gossypium hirsutum* L.) identifies candidate gene signatures in response to aflatoxin producing fungus Aspergillus flavus" , PLoS ONE, 10 (2015) e0138025.
Bhatnagar-Mathur, et al. "Biotechnological advances for combating Aspergillus flavus and aflatoxin contamination in crops" Plant Sci., 234 (2015) 119-132.
Brown, et al. "Living maize embryo influences accumulation of aflatoxin in maize kernels" J Food Protect, 56 (Nov. 1, 1993) 967-971.
Cary, et al. "Developing resistance to aflatoxin in maize and cottonseed" Toxins (Basel), 3 (Jun. 2011) 678-696.
Chen, et al. "Discovery and confirmation of genes/proteins associated with maize aflatoxin resistance" World Mycotoxin Journal, 8 (2015) 211-224.
DeGray, et al. "Expression of an antimicrobial peptide via the chloroplast genome to control phytopathogenic bacteria and fungi" Plant Physiol., 127 (2001) 852-862.
DeLucca, et al. "Fungicidal properties, sterol binding, and proteolytic resistance of the synthetic peptide D4E1" Canadian Journal of Microbiology, 44 (1998) 514-520.
Edwards, et al. "Contribution of amphipathicity and hydrophobicity to the antimicrobial activity and cytotoxicity of beta-hairpin peptides" ACS Infect Dis, 2 (2016) 442-450.
Frame, et al. "Genetic transformation using maize immature zygotic embryos" Methods Mol Biol, Springer Science +Business Media, LLC, Clifton, N.J., Jan. 2011, pp. 327-341.
Ganz, T. "Defensins: antimicrobial peptides of innate immunity" Nat Rev Immune, 3 (Sep. 2003) 710-720.
Kamo, et al. "Expression of a synthetic antimicrobial peptide, D4E1, in Gladiolus plants for resistance to Fusarium oxysporum f. sp. Gladioli" Plant Cell Tiss Organ Cult, 121 (2015) 459-467.
Liu, et al. "Response of transgenic Royal Gala apple (*Malus x domestica* Borkh.) shoots carrying a modified cecropin MB39 gene, to Erwinia amylovora" Plant Cell Rep., 20 (Published online May 1, 2001) 306-312.

(Continued)

*Primary Examiner* — Jason Deveau Rosen
(74) *Attorney, Agent, or Firm* — Edwin S. Flores; Daniel J. Chalker; Chalker Flores, LLP (57) ABSTRACT

*Aspergillus flavus* is an opportunistic, saprophytic fungus that infects maize and other fatty acid-rich food and feed crops and produces toxic and carcinogenic secondary metabolites known as aflatoxins. In vitro studies showed a five-fold increase in antifungal activity of AGM182 (vs. tachyplesin1) against *A. flavus*. Transgenic maize plants expressing AGM182 under maize Ubiquitin-1 promoter were produced through *Agrobacterium*-mediated transformation. PCR products confirmed integration of the AGM182 gene, while RT-PCR of maize RNA confirmed the presence of AGM182 transcripts. Maize kernel screening assay using a highly aflatoxigenic *A. flavus* strain (AF70) showed up to 72% reduction in fungal growth in the transgenic AGM182 seeds compared to isogenic negative control seeds.

19 Claims, 7 Drawing Sheets
Specification includes a Sequence Listing.

(56) References Cited

OTHER PUBLICATIONS

Majumdar, et al. "RNA Interference (RNAi) as a potential tool for control of mycotoxin contamination in crop plants: Concepts and considerations" Frontiers in Plant Science, 8 (published Feb. 14, 2017).

Masanga, et al., Downregulation of transcription factor aflR in Aspergillus flavus confers reduction to aflatoxin accumulation in transgenic maize with alteration of host plant architecture, Plant Cell Rep., 34 (2015) 1379-1387.

Mentag, et al. "Bacterial disease resistance of transgenic hybrid poplar expressing the synthetic antimicrobial peptide D4E1" Tree Physiology, 23 (published Mar. 17, 2003) 405-411.

Mitchell, et al. "Potential economic losses to the USA corn industry from aflatoxin contamination" Food Additives & Contaminants: Part A, 33 (Mar. 2016) 540-550.

Miyata, et al. Antimicrobial Peptides, Isolated from Horseshoe Crab Hemocytes, Tachyplesin II, and Polyphemusins I and II: Chemical Structures and Biological Activity, Journal of Biochemistry, 106 (1989) 663-668.

Montesinos, E. "Antimicrobial peptides and plant disease control" FEMS Microbiol. Lett., 270 (Mar. 2007) 1-11.

Munkvold, G.P. "Cultural and genetic approaches to managing mycotoxins in maize" Annu. Rev. Phytopathol., 41 (May 2003) 99-116.

Owens, et al. "A single amino acid substitution in the antimicrobial defense protein cecropin b is associated with diminished degradation by leaf intercellular fluid" Mol.Plant-Microbe Interact., 10 (1997) 525-528.

Rahnamaeian, M. "Antimicrobial peptides" Plant Signaling & Behavior, 6 (Sep. 2011) 1325-1332.

Rajasekaran, et al. "Disease resistance conferred by the expression of a gene encoding a synthetic peptide in transgenic cotton (*Gossypium hirsutum* L.) plants" Plant Biotechnol. J., 3 (2005) 545-554.

Rajasekaran, et al. Evaluation of resistance to aflatoxin contamination in kernels of maize genotypes using a GFP-expressing Aspergillus flavus strain World Mycotoxin Journal, 6 (2013) 151-158.

Rogers, J.C. "Two barley alpha-amylase gene families are regulated differently in aleurone cells" J. Biol. Chem., 260 (1985) 3731-3738.

Schubert, et al. "Thanatin confers partial resistance against aflatoxigenic fungi in maize (*Zea mays*)" Transgenic Res., 24 (2015) 885-895.

Schwab, et al. "In vitro activities of designed antimicrobial peptides against multidrug-resistant cystic fibrosis pathogens" Antimicrob. Agents Chemother., 43 (Jun. 1999) 1435 1440.

Thakare, et al. "Aflatoxin-free transgenic maize using host-induced gene silencing" Science Advances, 3 (Mar. 10, 2017) 1-8.

Udomkun, et al. "Innovative technologies to manage aflatoxins in foods and feeds and the profitability of application—A review, Food Control" 76 (Jan. 2017) 127-138.

Wang, et al. "APD3: the antimicrobial peptide database as a tool for research and education" Nucleic Acids Res., 44 (published online Nov. 23, 2015) D1087-1093.

Williams, et al. "Identifying and developing maize germplasm with resistance to accumulation of aflatoxins" World Mycotoxin Journal, 8 (Jan. 2015) 193-209.

Wu, F. "Mycotoxin reduction in Bt corn: potential economic, health, and regulatory impacts" Transgenic Res., 15 (Sep. 2006) 277-289.

Rajaskeran, et al. "Control of Aspergillus flavus growth and aflatoxin production in transgenic maize kernels expressing a tachyplesin-derived synthetic peptide, AGM182" Plant Science 270 (available online Feb. 21, 2018) pp. 150-156.
Rajaskeran, et al. "Disease resistance conferred by the expression of a gene encoding a synthetic peptide in transgenic cotton (*Gossypium hirsutum* I.) plants" Plant Biotechnology Journal (2005) 3, pp. 545-554.
Shigenaga, et al. "Antimicrobial Tachyplesin Peptide Precursor cDNA Cloning and Cellular Localization in the Horseshoe Crab (*Tachypleus tridentatus*)" The Journal of Biological Chemistry, vol. 265, No. 34, Issue Dec. 5, 1990, pp. 21350-21354.

* cited by examiner

SEQUENCE LISTING

```
<160> NUMBER OF SEQ ID NOS: 12

<210> SEQ ID NO 1
<211> LENGTH: 17
<212> TYPE: PRT
<213> ORGANISM: Artificial Sequence
<220> FEATURE:
<223> OTHER INFORMATION: Synthetic

<400> SEQUENCE: 1

Lys Trp Cys Phe Arg Val Cys Tyr Arg Gly Ile Cys Tyr Arg Arg Cys
1               5                   10                  15

Arg

<210> SEQ ID NO 2
<211> LENGTH: 18
<212> TYPE: PRT
<213> ORGANISM: Artificial Sequence
<220> FEATURE:
<223> OTHER INFORMATION: Synthetic

<400> SEQUENCE: 2

Lys Ile Lys Ala Arg Leu Cys Leu Gly Lys Phe Cys Ile Lys Ala Arg
1               5                   10                  15

Leu Lys
```

<210> SEQ ID NO 3
<211> LENGTH: 129
<212> TYPE: DNA
<213> ORGANISM: Artificial Sequence
<220> FEATURE:
<223> OTHER INFORMATION: Synthetic

<400> SEQUENCE: 3

```
atggccaaca agcatctgtc gctctccctg ttcctcgtgc tccttggcct gtctgccagc    60
ctcgctagtg gcaagattaa agcgcgcctg tgcctgggaa agttctgtat aaaggcgcgg   120
ctcaagtag                                                           129
```

<210> SEQ ID NO 4
<211> LENGTH: 42
<212> TYPE: PRT
<213> ORGANISM: Artificial Sequence
<220> FEATURE:
<223> OTHER INFORMATION: Synthetic

<400> SEQUENCE: 4

```
Met Ala Asn Lys His Leu Ser Leu Ser Leu Phe Leu Val Leu Leu Gly
1               5                   10                  15

Leu Ser Ala Ser Leu Ala Ser Gly Lys Ile Lys Ala Arg Leu Cys Leu
            20                  25                  30

Gly Lys Phe Cys Ile Lys Ala Arg Leu Lys
        35                  40
```

<210> SEQ ID NO 5
<211> LENGTH: 6
<212> TYPE: PRT
<213> ORGANISM: Artificial Sequence
<220> FEATURE:
<223> OTHER INFORMATION: Synthetic

<400> SEQUENCE: 5

```
Cys Leu Gly Lys Phe Cys
1               5
```

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

```
Cys Tyr Arg Gly Ile Cys
1               5
```

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7

```
atggccaaca agcatctgtc                                                20
```

<210> SEQ ID NO 8
<211> LENGTH: 20
<212> TYPE: DNA
<213> ORGANISM: Artificial Sequence 
```
<220> FEATURE:
<223> OTHER INFORMATION: Synthetic

<400> SEQUENCE: 8
ccgcgccttt atacagaact                                               20

<210> SEQ ID NO 9
<211> LENGTH: 18
<212> TYPE: DNA
<213> ORGANISM: Artificial Sequence
<220> FEATURE:
<223> OTHER INFORMATION: Synthetic

<400> SEQUENCE: 9
tggccaacaa gcatctgt                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetic

<400> SEQUENCE: 10
acaggcgcgc tttaatct                                                 18

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ggcttggctt aaaggaaggt                                               20

<210> SEQ ID NO 12
<211> LENGTH: 21
<212> TYPE: DNA
<213> ORGANISM: Artificial Sequence
<220> FEATURE:
<223> OTHER INFORMATION: Synthetic

<400> SEQUENCE: 12
tcagtccaac ttccagaatg g                                             21
```

TRANSGENIC CORN WITH ANTIFUNGAL PEPTIDE AGM182 (DN:0113.18)

CROSS-REFERENCE TO RELATED APPLICATIONS

This application is a continuation of U.S. patent application Ser. No. 16/134,336, filed Sep. 18, 2018, the entire contents of which are incorporated herein by reference.

REFERENCE TO SEQUENCE LISTING SUBMITTED VIA EFS-WEB

This application includes an electronically submitted sequence listing in .txt format. The .txt file contains a sequence listing entitled "2018-10-29 NEXION ST25.txt" created on Oct. 29, 2018 and is 2,985 bytes in size. The sequence listing contained in this .txt file is part of the specification and is hereby incorporated by reference herein in its entirety.

FIELD OF THE INVENTION

Control of *Aspergillus flavus* growth and aflatoxin production in transgenic maize kernels expressing a tachyplesin-derived synthetic peptide, AGM182.

BACKGROUND OF THE INVENTION

*Aspergillus flavus* is an opportunistic, saprophytic fungus that infects fatty acid-rich food and feed crops including maize [1]. Upon infection, the fungus produces toxic and carcinogenic secondary metabolites known as aflatoxins. Aflatoxin contamination of maize has an economic impact of approximately $163 million/year in the U.S. [2]. With rapid change in global climate, it is predicted that aflatoxin contamination could cause losses to the maize industry up to US$1.68 billion per year in the United States [3]. Besides crop loss, the adverse effect of aflatoxins on human and animal health is acute [1] that can result in liver cancer. Different approaches are being explored to alter genetically, through either traditional breeding efforts or other gene manipulation techniques, maize varieties for increased resistance to preharvest aflatoxin contamination [4]. Previously published reports indicate the usefulness of naturally occurring antimicrobial peptides (AMPs), also known as host defense peptides, such as cecropin, melittin, magainin, defensin and protegrin for controlling a variety of phytopathogens [5-9].

AMPs are evolutionarily highly conserved components of the innate immune system, which provide the first line of defense against invading pathogens [10]. Their significance in host defense is underscored in plants and insects as these can live in bacterial environments without the ability to produce lymphocytes and antibodies. AMPs have direct antimicrobial activities and kill Gram-negative and -positive bacteria, as well as fungi and protozoa [11-14]. They often assume secondary structures in the form of amphipathic α-helices or partial β-pleated sheets that latter being 'conformationally-locked' by disulfide linkages. AMPs exert biological activity by interacting electrostatically and perturbs the pathogen's membrane thereby impairing its function as a barrier [15]. Ergosterol, the membrane sterol found almost exclusively in fungi and present in conidial walls is a highly selective target of AMPs and this interaction leads to lytic membrane disruption [16]. Mammalian cells, which contain more zwitterionic phospholipids framed with cholesterol and cholesterol esters, are much less disturbed by AMP interactions. This targeting effect and direct contact disruption of the pathogen's membrane makes resistance less likely to develop [17]. Unfortunately, natural peptides are subject to rapid degradation in the cytoplasm reducing their effectiveness in planta. Designed antimicrobial peptides (dAMPs) are laboratory-synthesized peptides that have been rationally and chemically designed from naturally occurring AMPs. Based upon the functions and structure in naturally occurring AMPs, structural algorithms have been developed that have added numerous variations to the structural repertoire by design, laboratory created peptides have demonstrated increased potency, efficacy, safety, specificity and reduced toxicity in comparison to their natural templates [7, 18]. Synthetic peptides, which are fairly resistant to cytoplasmic degradation [16], are useful in controlling a broad-spectrum of plant pathogens including the saprophytic fungus, *A. flavus* [19, 20]. The effectiveness of synthetic peptides such as D4E1, D2A21 or MS199 expressed in transgenic cotton and other crops for controlling *Aspergillus* and other microbial pathogens has been demonstrated in our laboratory and elsewhere (see [21]). Synthetic peptides, which can be designed to be fairly resistant to cytoplasmic degradation, are also effective in controlling a broad-spectrum of microbial plant pathogens including the mycotoxin-producing fungal species—*Aspergillus* and *Fusarium*. These peptides also exhibit no toxicity against mammals and non-target beneficial organisms [22, 23]. We had documented earlier the effectiveness of a cecropin-based synthetic, lytic peptide, D4E1, in controlling *A. flavus* infection in transgenic cottonseed in situ and in planta [20]. Schubert et al. [24] showed partial resistance against *Aspergillus* in transgenic maize expressing a recombinant thanatin peptide. We have recently evaluated another group of synthetic peptides, modelled after tachyplesin1—a defensin-like peptide [25], found in the acid extract of hemocytes from the Japanese horseshoe crab (*Tachypleus tridentatus*), against

*flavus* [26]. In this report, we describe the design and synthesis of a tachyplesin-based antimicrobial peptide AGM182. We tested its efficacy in vitro to inhibit *A. flavus* growth as compared to the native tachyplesin1. We also produced transgenic maize lines expressing the synthetic peptide AGM182 and assayed the seeds for anti-*A. flavus* activity and determined aflatoxin levels in transgenic lines. Reduction of aflatoxin contamination through transgenic expression of a synthetic peptide in an important food crop such as maize is detailed in this report. The results presented here show the effectiveness of computational and synthetic biology to rationally design, synthesize, and validate an AMP against *A. flavus* that is effective in reducing fungal growth and aflatoxin contamination in a major crop like maize.

BRIEF DESCRIPTION OF THE INVENTION

*Aspergillus flavus* is an opportunistic, saprophytic fungus that infects maize and other fatty acid-rich food and feed crops and produces toxic and carcinogenic secondary metabolites known as aflatoxins. Contamination of maize with aflatoxin poses a serious threat to human health in addition to reducing the crop value leading to a substantial economic loss. Here we report designing a tachyplesin1-derived synthetic peptide AGM182 and testing its antifungal activity both in vitro and in planta. In vitro studies showed a five-fold increase in antifungal activity of AGM182 (vs. tachyplesin1) against *A. flavus*. Transgenic maize plants expressing AGM182 under maize Ubiquitin-1 promoter were produced through *Agrobacterium*-mediated transformation. PCR products confirmed integration of the AGM182 gene, while RT-PCR of maize RNA confirmed the presence of AGM182 transcripts. Maize kernel screening assay using a highly aflatoxigenic *A. flavus* strain (AF70) showed up to 72% reduction in fungal growth in the transgenic AGM182 seeds compared to isogenic negative control seeds. Reduced fungal growth in the AGM182 transgenic seeds resulted in a significant reduction in aflatoxin levels (76-98%). The results presented here show the power of computational and synthetic biology to rationally design and synthesize an antimicrobial peptide against *A. flavus* that is effective in reducing fungal growth and aflatoxin contamination in an economically important food and feed crop such as maize.

More specifically, the present invention is referred to a method to produce transgenic maize lines expressing synthetic peptide, AGM182, the method comprising the steps of:

a. designing a gene AGM182 comprising 129 bp fragment from naturally occurring antimicrobial peptide tachyplesin 1, the designing comprising: [0009] b. eliminating second disulfide linkage of peptide tachyplesin 1; and [0010] c. replacing a sequence from the peptide tachyplesin 1 by amino acid residues that results in amphipathic β-sheet conformation with higher positive charge density, higher hydrophobicity, anti-fungal activity and stability; [0011] d. cloning the AGM182 gene into a pMCG 1005 plasmid under a constitutive Ubi-1 (maize) promoter; [0012] e. incorporating a maize alcohol dehydrogenase-1 (Adh-1) intron into the upstream of the AGM182 start codon, wherein the Adh-1 intron improves the expression of the AGM182 gene; [0013] f fusing a barley alpha amylase signal peptide (BAAS) to the N-terminal end of the AGM182 gene, wherein the BAAS peptide increases the efficiency of AGM182 excretion from the host cell to the cell wall; [0014] g. producing the transgenic maize lines through an *Agrobacterium* EHA101-mediated transformation of the AGM182 gene into immature maize embryos.

BRIEF DESCRIPTION OF THE DRAWINGS

FIG. 1 (SEQ ID NOS: 1 and 2) is a schematic diagram showing the physical properties of both peptides compared by casting the single letter amino acid codes (top row) into Molly (bottom row) [36, 42], a glyph-based design tool.

FIGS. 2A, 2B shows three dimensional depictions of the tachyplesin1 (FIG. 2A, SEQ ID NO: 2) and AGM182 (FIG. 2B, SEQ ID NO: 1) were generated in PyMol, a molecular visualization system maintained and distributed by Schrodinger, a computational chemistry company (Cambridge, Mass.).

FIGS. 3A to 3C show AGM182 gene and vector information. FIG. 3A shows the AGM182 nucleotide sequence (SEQ ID NO:3), FIG. 3B shows the amino acid sequence (SEQ ID NO:4), and FIG. 3C is a pMCG1005 vector diagram containing AGM182 expression cassette used for maize transformation using the *Agrobacterium* strain.

FIG. 4 is a graph that shows the inhibitory activity in vitro of tachyplesin1 and tachyplesin-based synthetic peptide, AGM182 against pre-germinated conidia of *A. flavus*. AGM182 showed a better inhibitory activity ($IC_{50}$=2.5 μM) than tachyplesin1 against *A. flavus* ($IC_{50}$=12.5 μM). Average means of three independently replicated assays.

FIGS. 5A and 5B. Molecular analyses of AGM182 expressing transgenic maize plants. (FIG. 5A) PCR confirmation of transgenic plants containing AGM182 gene (129 bp diagnostic DNA fragment; +ve=plasmid control; C=isogenic negative control; (FIG. 5B) AGM182 expression (90 bp product) in the seeds of transgenic lines [vs. negative control (C)] using RT-PCR. Maize ribosomal structural gene (Rib), GRMZM2G024838 [33], was used as house-keeping gene. (132 bp product). NEB 2 log DNA ladder was used as a DNA marker.

FIG. 6 shows GFP fluorescence emanating from the *A. flavus* strain 70-GFP in transgenic kernels after one week of bioassay. Isogenic negative control kernels (neg) were used to evaluate the fungal infection and spread in transgenic kernels (Lines 2-5). Up to 10 kernels were screened for each line under the fluorescent microscope and a representative kernel is shown here.

FIGS. 7A and 7B show *A. flavus* infection, growth, and aflatoxin production after 7 d in a Kernel Screening Assay. FIG. 7A shows the average of 12 biological replicates and each replicate contained at least four kernels. GFP quantification (in Relative Fluorescence Units) which indicates fungal growth and FIG. 7B shows aflatoxin levels in transgenic *A. flavus*-infected $T_3$ maize kernels (Lines 1-6 as compared with an isogenic negative control). Mean separation was done by Dunnett's posttest after ANOVA. Levels of significant reduction is denoted by asterisks (=95%; *=99% probability levels). Error bars indicate standard error of means for four randomized biological replicates.

DETAILED DESCRIPTION OF THE INVENTION

FIG. 1 (SEQ ID NOS: 1 and 2) shows the physical properties of both peptides compared by casting the single letter amino acid codes (top row) into Molly (bottom row) [36, 42], a glyph-based design tool. Cyan color represents those amino acids that are hydrophobic while those that are hydrophilic retain a magenta color. Disulfide linkages are denoted by the green lines connecting the relevant cysteines, which are yellow in color. While a similar 'central bubble' has been maintained in the AGM182 (CLGKFC)(SEQ ID NO: 5) compared to that of tachyplesin1 (CYRGIC)(SEQ ID NO: 6), the second disulfide linkage of tachyplesin1 has been eliminated in AGM182 and replaced by a sequence that assumes an amphipathic beta-sheet conformation with maximized positive charge density. This property has been demonstrated to enhance anti-fungal activity of dAMP peptides [19, 36]. The red dots on AGM182 denote the differences in amino acid sequence compared to tachyplesin1.

The main highlights of the present invention can be summarized as:

Designed the synthetic peptide AGM182 modeled after the naturally occurring tachyplesin 1.

AGM182 was five-times more effective in controlling *Aspergillus flavus* compared to tachyplesin 1.

Transgenic maize plants expressing the synthetic peptide AGM182 were produced and advanced to third generation by selfing.

Kernel Screening Assay showed significant reduction in fungal growth (72%) and spread inside transgenic kernels.

Concomitant, significant reduction in aflatoxin levels (76-98%) was also achieved in transgenic kernels.

The abbreviations to be used in the present specification are: RB=right border, LB=left border, Ubi-1=maize Ubiquitin) promoter (constitutive), Int=intron (maize alcohol dehydrogenase-1; Adh1), AGM182=gene of interest; BAAS=barley alpha amylase signal peptide, ocs (octopine synthase)=terminator, nos (nopaline synthase)=terminator, 4×35S=constitutive cauliflower mosaic virus promoter, Bar=phosphinothricin acetyltransferase gene for BASTA herbicide resistance.

Materials and Methods

In Silico Analysis of AGM182

Figure 1:
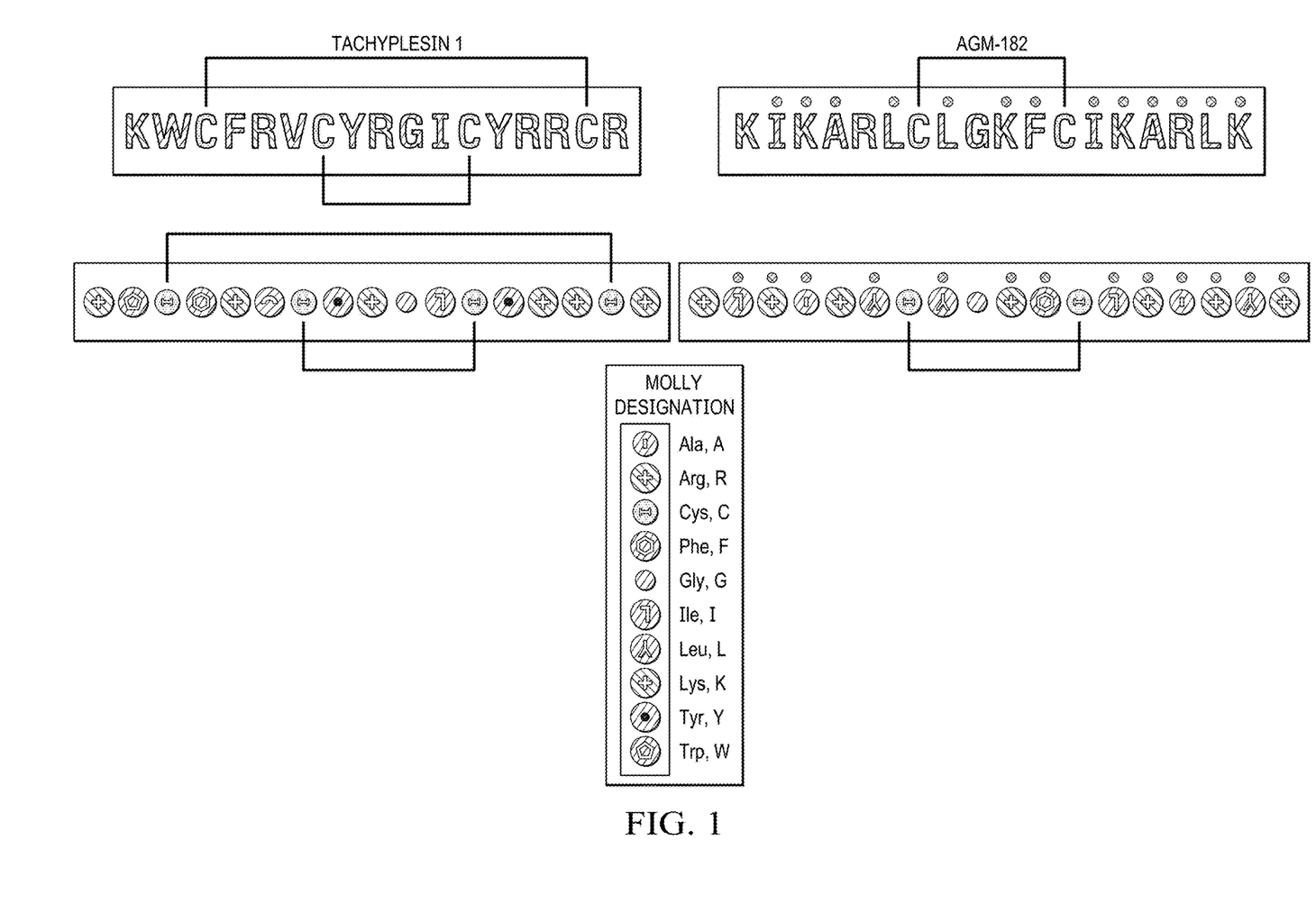
Figure 2A:
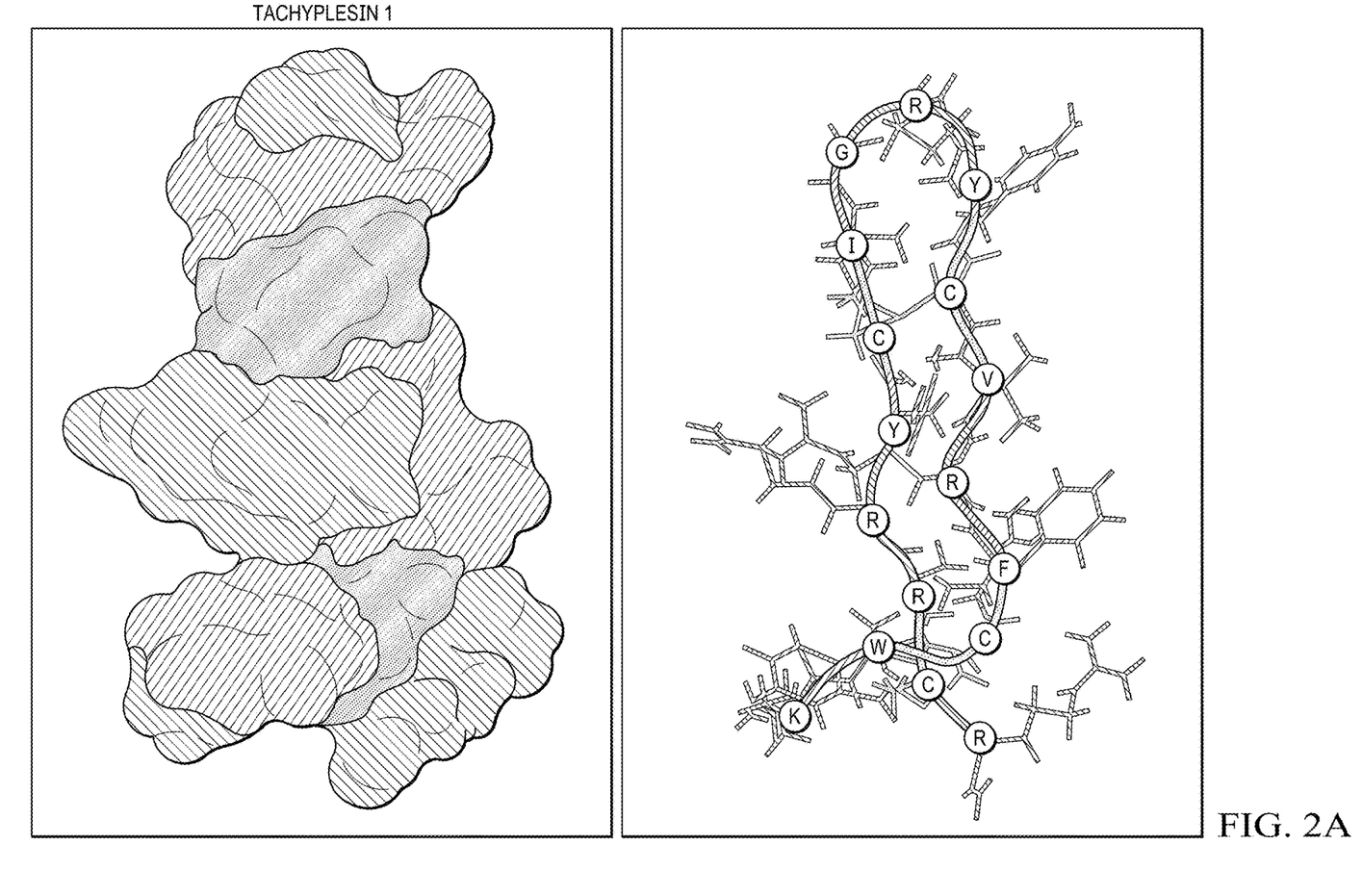
Figure 2B:
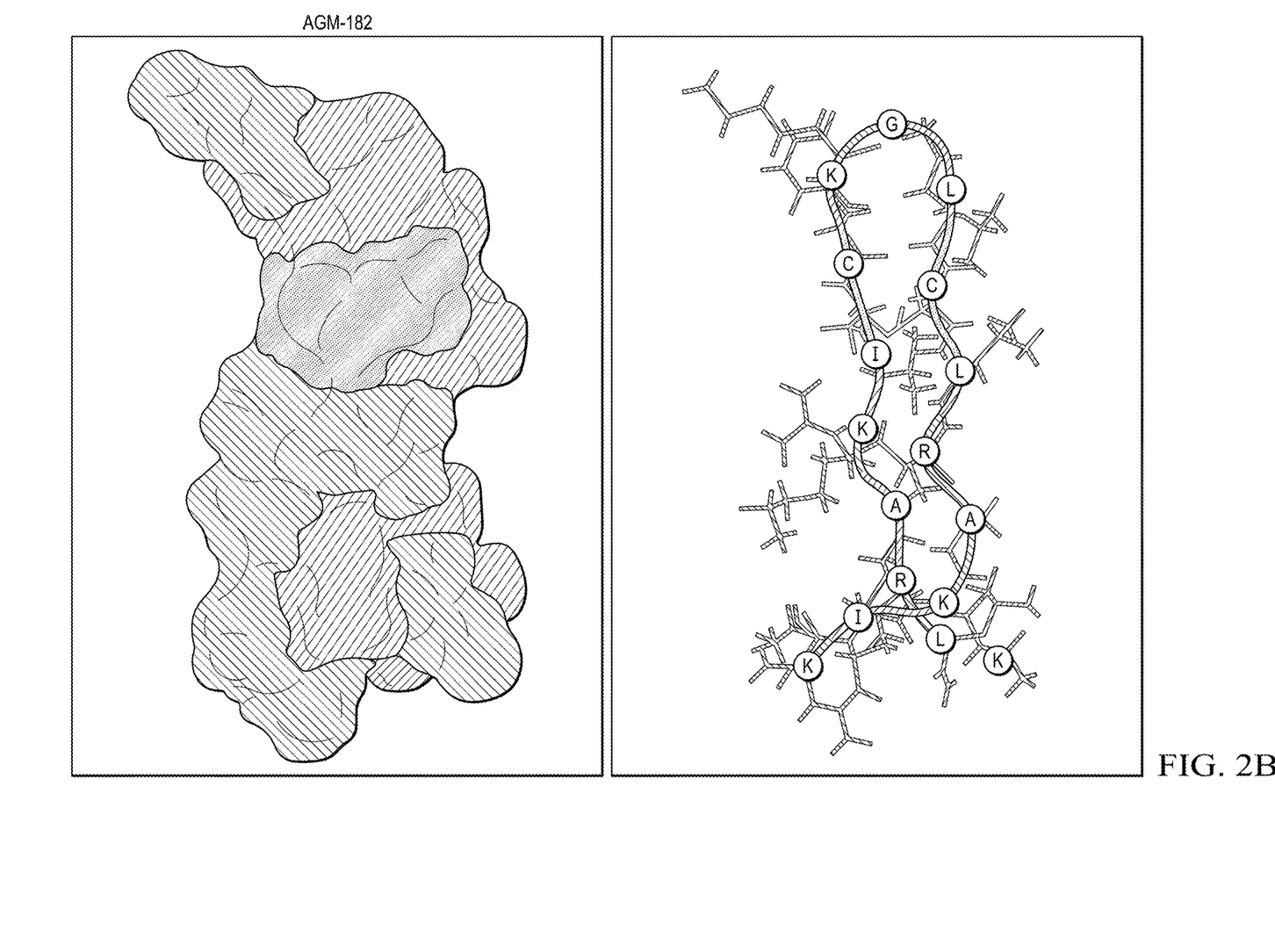

The synthetic peptide AGM182 used in the current study were designed based on the known antimicrobial peptide tachyplesin1 (FIGS. 1 and 2). The 3D structures of the AMPs were generated using PyMol software, maintained and distributed by Schrodinger, a computational chemistry company (Cambridge, Mass.). The AMPs were analyzed using the AMP predictor tools, 'Antimicrobial Peptide Calculator and Predictor' (Antimicrobial Peptide Database with APD3 algorithm; aps.unmc.edu/AP/ [27]. Tachyplesin1 was synthesized by Bachem (Bubendorf, Switzerland) and AGM182 synthetic peptide (AgroMed/Nexion Biosciences Ltd, Riva, Md.) was synthesized by Biomatik (Cambridge, Ont, Canada), both with a purity of >95% as obtained by the analyses of HPLC and Mass Spectrometry data provided by the manufacturers.

Plasmid Constructs and Maize Transformation

A 129 bp fragment of the AGM182 gene (SEQ ID NO:3) was synthesized (IDT; Coralville, Iowa) and cloned in to the pMCG 1005 vector [28] (provided by Dr. Kan Wang, IA State University). The synthetic AGM182 gene (codon optimized for expression in maize) was expressed under the constitutive Ubi-1 (maize) promoter present in the plant destination vector. The maize alcohol dehydrogenase-1 (Adh1) intron present in the transgene cassette (upstream of the AGM182 start codon) was incorporated to improve the expression of AGM182 in maize (monocot) and the barley alpha amylase signal peptide (BAAS) was fused to the N-terminal end of the AGM182 gene (FIG. 3C) to increase the efficiency of AGM182 (peptide) excretion from the host cells to the cell wall [29]. *Agrobacterium* EHA101-mediated transformation of immature maize (*Zea mays* L. Hi-II) embryos was accomplished through the Plant Transformation Facility at the Iowa State University [30]. Maize seedlings were grown at 25° C. under 16 h photoperiod (80).

µmol m-2 s-1) in a growth chamber for 4 weeks and then moved in to the greenhouse in 5-gallon (19 L) pots [31]. Transgenic plants from independently transformed events were grown in moist soil mix containing 3 parts Scott's 360 Metro-Mix (Scotts Company, Marysville, Ohio) and 1 part perlite in 7.5 cm pots and were selfed to obtain $T_3$ generation kernels. Isogenic maize lines that went through transformation process but tested negative by PCR and herbicide assay [31] were used as negative controls.

Fungal Strain and Bioassay with Peptides

*Aspergillus flavus* 70-GFP [32] was grown at 31° C. on V8 medium (5% V8 juice, 2% agar, pH 5.2). Spores from 6-day old cultures were suspended in 0.02% Triton X-100; the conidial concentration was determined with a hemocytometer and adjusted to $4×10^6$ conidia ml-1.

Peptides were freshly dissolved in sterilized water and used for antifungal bioassays as reported [19]. Briefly, pre-germinated conidial suspensions ($4×10^6$ conidia ml$^{-1}$) of *A. flavus* 70-GFP were treated with the peptides at 0-25 µM concentrations for 60 min before spreading on Potato Dextrose Agar plates (9 cm day). Fungal colonies were enumerated following incubation at 30° C. for 24 h.

PCR Screening of Transgenic Maize Kernels

Maize seeds were flash frozen and ground using a 2010 Geno/Grinder (SPEX SamplePrep, Metuchen, N.J.). Transgenic plants were screened through PCR using 'Phire Plant Direct PCR Kit' (ThermoFisher Scientific, Waltham, Mass.) according to the manufacturer's protocol. The screening primers used in this study were, AGM182_F1: 5'-ATGGC-CAACAAGCATCTGTC-3' (SEQ ID NO: 7) and AGM182_R1: 5'-CCGCGCCTTTATACAGAACT-3' (SEQ ID NO: 8). A 51° C. annealing temperature and 10 s elongation time were used to amplify a 129 bp DNA fragment to confirm the presence of the AGM182 gene in the transgenic maize plants.

RNA Isolation, cDNA Synthesis, and Semi-Quantitative RT-PCR

Pulverized maize seeds were used for RNA isolation using the Spectrum™ Plant Total RNA kit' (Sigma-Aldrich, St Louis, Mo.). cDNA was synthesized using iScript™ cDNA synthesis kit (Bio-Rad, Hercules, Calif.) according to the manufacturer's protocol. Semi-quantitative RT-PCR was performed using T100™ thermal cycler system (Bio-Rad) and Phusion® High-Fidelity DNA Polymerase (New England Biolabs, Ipswich, Mass.). The thermocycling conditions included a
pre-incubation at 98° C. for 30 s followed by 30 cycles of 98° C. for 10 s (denaturation), 51.5° C. for 30 s (primer annealing), 72° C. for 5 s (elongation), and a final extension step at 72° C. for 5 min. The primers used for RT-PCR of AGM182 in transgenic plants are qAGM182-F2 5'-TGGC-CAACAAGCATCTGT-3' SEQ ID NO: 9) and qAGM182-R2 5'-ACAGGCGCGCTTTAATCT-3' (SEQ ID NO: 10) and maize ribosomal structural gene (Rib), GRMZM2G024838 [33], qRib-F 5'-GGCTTGGCT-TAAAGGAAGGT-3' (SEQ ID NO: 11) and qRib-R 5'-TCAGTCCAACTTCCAGAATGG-3' (SEQ ID NO: 12).

Kernel Screening Assay

Undamaged $T_3$ maize and negative control seeds were surface-sterilized with 70% ethanol and subjected to the Kernel Screening Assay (KSA) [32]. Surface-sterilized seeds were briefly immersed in a $4×10^6$ conidial inoculum and incubated in the dark at 31° C. and high humidity (>95% RH). After seven days, four representative seeds were randomly chosen and photographed (bright field and fluorescence) using an Olympus SZH10 research stereomicroscope equipped with the Nikon Digital Camera DXM1200.

GFP Fluorescence and Aflatoxin Analysis

To quantify fungal fluorescence pulverized *A. flavus* infected maize seeds (50 mg FW) were extracted in 0.5 ml of Sorenson's phosphate buffer (pH 7.0). The samples were vortexed for 30 s followed by centrifugation at 10,000 g for 15 min. A 100 µl aliquot of the supernatant was transferred to each well of a 96 well plate and GFP fluorescence (excitation 485 nm, emission
535) were recorded using a plate reader (Biotek Synergy 4, Winooski, Vt.) [32, 34]. Relative Fluorescence Units (RFU) were normalized as percent values and used for statistical analysis from 12 biological replicates. Each replicate consisted of four randomly selected, PCR positive kernels. Following molecular analysis and GFP quantitation, seed samples were pooled together into four randomized replicates. Homogenates from three maize seeds were pooled, dried in a forced air oven (60° C.), and extracted with methylene chloride [35]. Sample residues were dissolved in 4.0 ml 80% methanol and total aflatoxin levels were measured with the FluoroQuant Afla Test Kit for Aflatoxin Analysis (Romer Labs, Union, Mo.).

Statistical Analysis

All data from two independent KSAs including fluorescence (12 biological replicates), and aflatoxin values (four randomized replicates) were subjected to one-way ANOVA and mean separation was performed using the Dunnett's posttest ($P<0.05$ or $<0.01$) using GraphPad Prism software (La Jolla, Calif.).

Results

Design and in Silico Analysis of AGM182

The synthetic AGM182 peptide was designed based on the naturally occurring Tachyplesin I peptide from Japanese horseshoe crab. Analysis of amino acids in the AGM182 shows increase in positive charge density (vs. Tachyplesin1). While a similar 'central bubble' (CLGKFC)(SEQ ID NO: 5) has been maintained in the AGM182 compared to that of Tachyplesin1 (CYRGIC)(SEQ ID NO: 6), the second disulfide linkage of Tachyplesin1 was eliminated in AGM182 and replaced by a sequence that results into an amphipathic β-sheet structure conformation with maximized positive charge density for improved antifungal activity FIG. 1. The three-dimensional structures of both Tachyplesin I and AGM-182 are shown in FIG. 2A (tachyplesin1 (SEQ ID NO: 2) and FIG. 2B (AGM182 (SEQ ID NO: 1)). The physical-chemical properties of both AMPs, that include length of the peptide, amino acid composition, charge, molecular weight, hydrophobicity, and Boman index. Hydrophobicity was significantly increased in the AGM182 peptide.

In Vitro Testing of Antimicrobial Activity of the Peptides

Figure 3A:
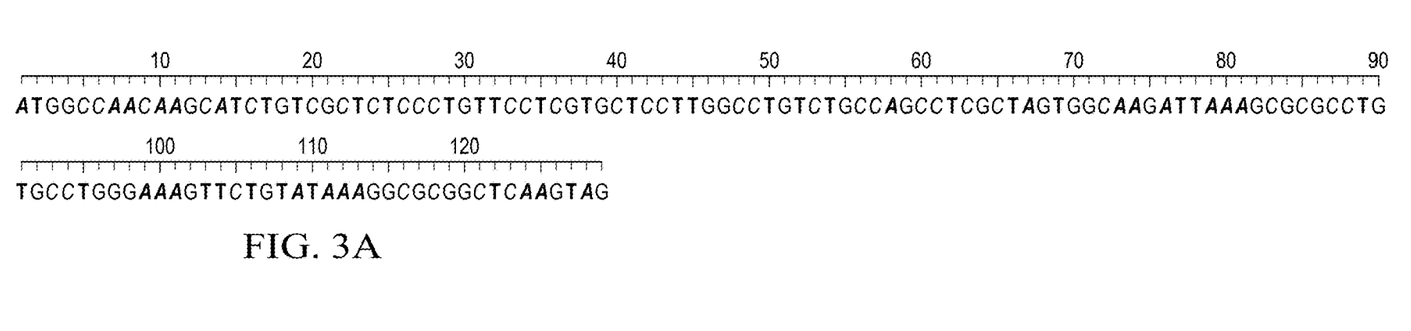
Figure 3B:
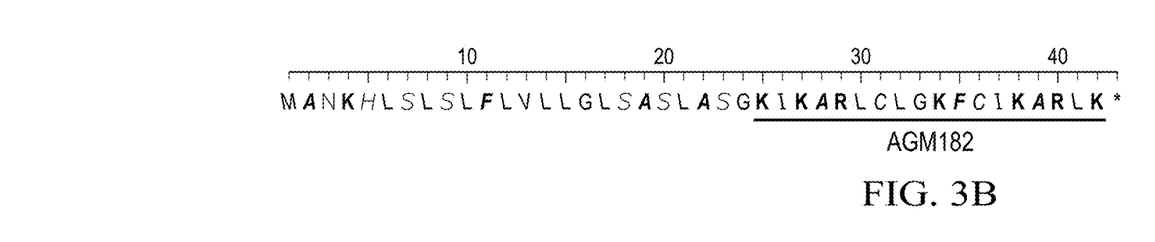
Figure 3C:
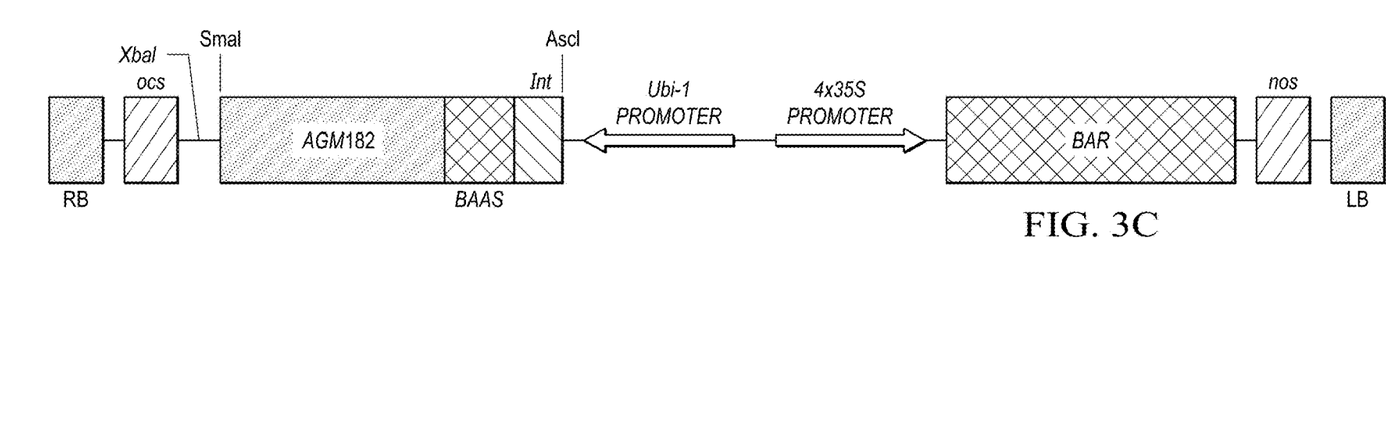
Figure 4:
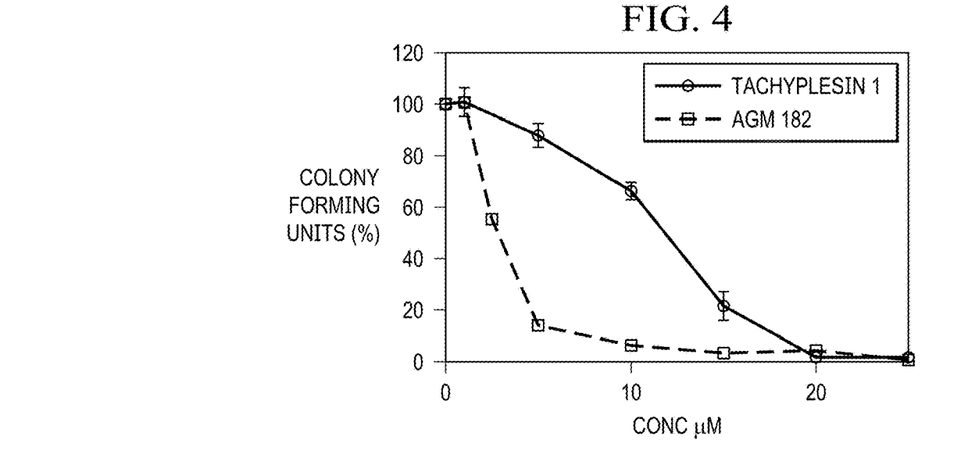

The synthetic peptide AGM182 was evaluated for activity against *A. flavus* in comparison to the native peptide tachyplesin1. AGM182 showed fivefold increase in its $IC_{50}$ value against *A. flavus* as compared to tachyplesin1 ($IC_{50}$=2.5 µM vs. 12.5 µM; FIG. 3C). No hemolysis of porcine blood cells was observed at all concentrations of AGM182 compared to 100% hemolysis with 0.1% Triton-X.

Maize Transformation and Molecular Screening of Transgenic Plants

Figure 5A:
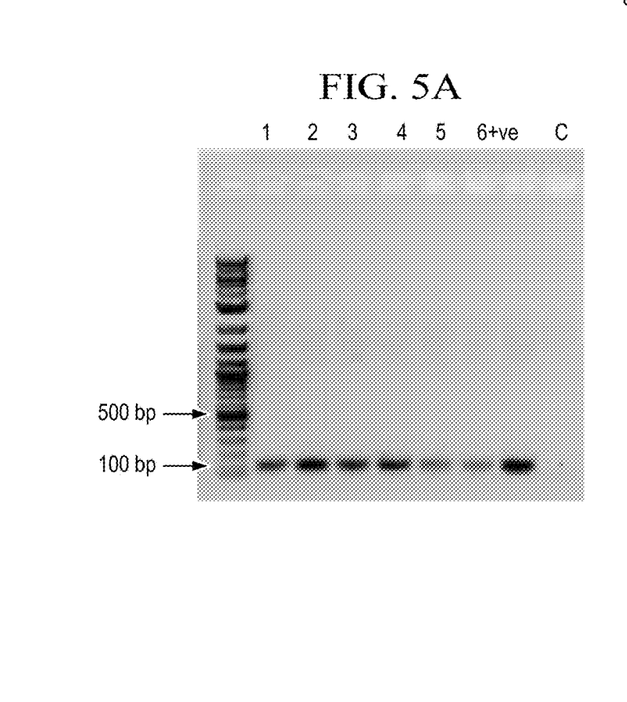
Figure 5B:
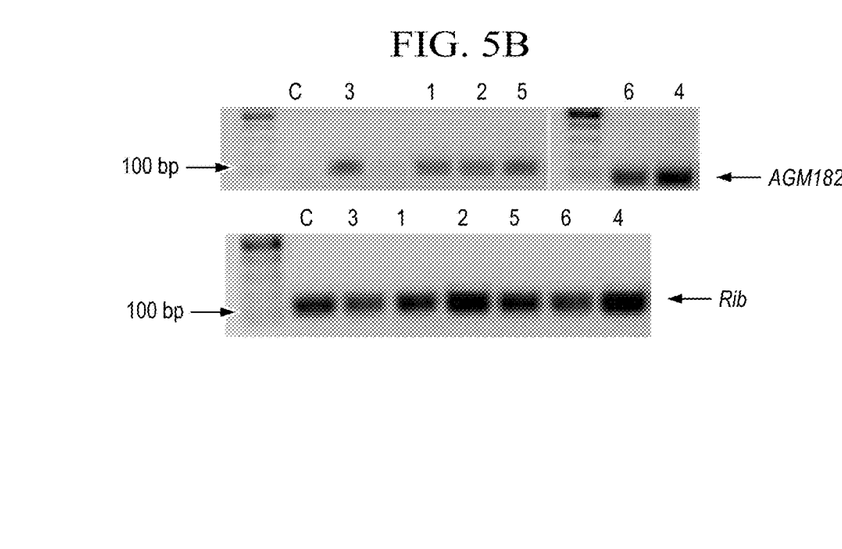

Transformation of maize (Hybrid Hi-II) was accomplished using the *Agrobacterium tumefaciens* EHA101-mediated transformation of immature embryos [31]. The codon-optimized synthetic AGM182 gene was expressed under the constitutive Ubi-1 promoter FIG. 3C. Thirteen independently transformed TO lines were generated and eleven $T_1$ lines were found positive for the presence of both the herbicide marker gene and AGM182. Eight $T_2$ lines were selected and advanced to $T_3$ generation in the greenhouse by selfing and only six lines expressing the AGM182 gene provided sufficient number of kernels for further assays. Transgenic maize plants did not exhibit any overt phenotype compared to isogenic negative or non-transformed control plants (data not shown). PCR screening of the transgenic maize seed showed the presence of 129 bp amplicon (AGM182 specific) in the AGM182 transgenic plants that was absent in the control plants (FIG. 5A). Expression analysis of the AGM182 transcripts in the AGM182 positive plants demonstrated substantial expression of this synthetic gene and no expression was observed in the control plants (FIG. 5A).

*A. flavus* Growth During Infection of Transgenic Seeds

Figure 6:
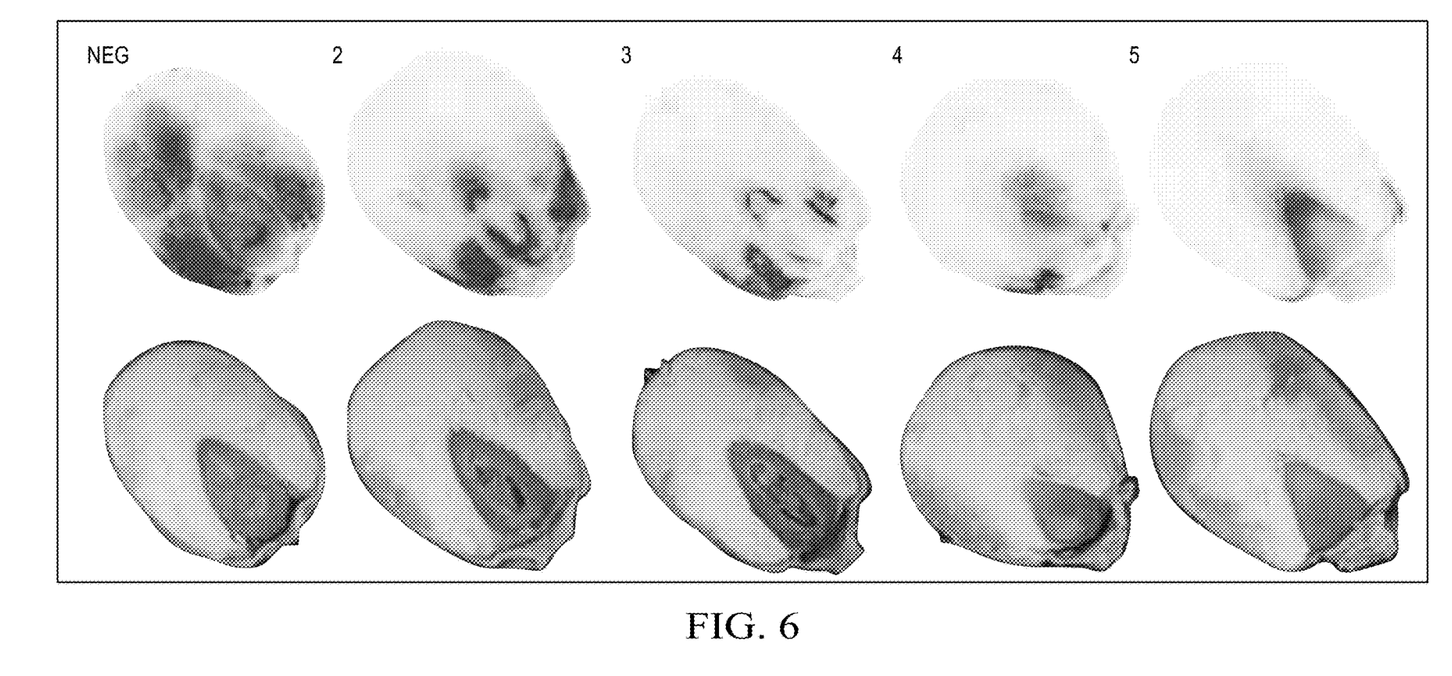
Figure 7A:
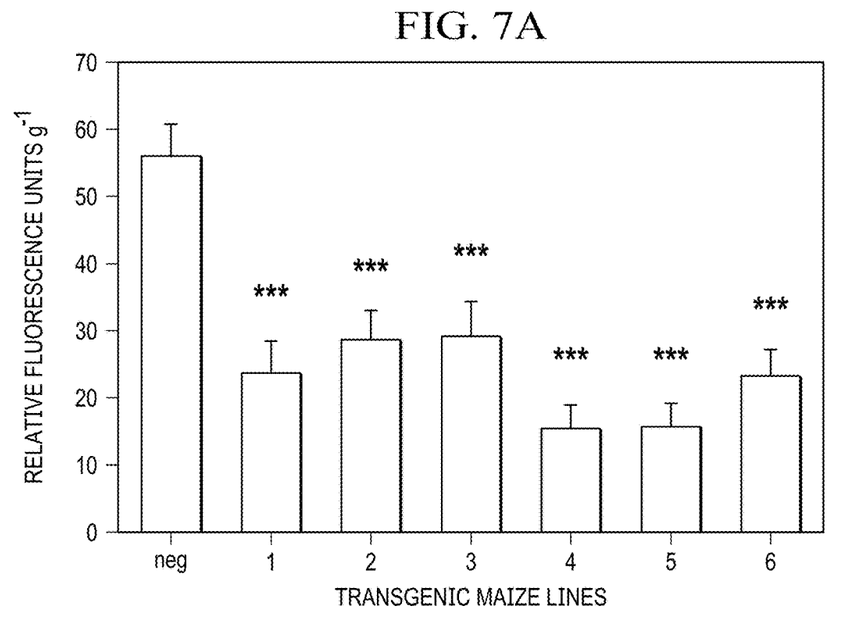

*A. flavus* growth was monitored in transgenic seeds using the KSA. Expression of the AGM182 gene in transgenic maize kernels resulted in a significant decrease in fungal growth as compared to the control (FIG. 6). GFP fluorescence, as an indicator of fungal growth inside the kernel embryo and/or endosperm positively correlated with the extent of fungal growth. AGM182-expressing maize kernels showed significant reduction in fungal growth (up to 72%) as indicated by the decrease in GFP fluorescence compared to the isogenic control (FIG. 7A).

Aflatoxin Production in Transgenic Kernels

Transgenic expression of the AGM182 gene in maize significantly reduced aflatoxin content in the transgenic lines as compared to the control. In general, between the two aflatoxins ($B_1$ and $B_2$) primarily detected in *A. flavus* infected maize kernels, aflatoxin $B_1$ is the predominant aflatoxin. The aflatoxin data presented here is the total amount of aflatoxins detected in the infected kernels. A significant reduction in aflatoxin levels (76-98%) was observed in the different AGM182 lines as compared to an isogenic negative control (FIG. 7B bottom). Among the six different AGM182 lines studied here, transgenic Line 4 had the lowest aflatoxin level in the seeds (60.0 ng·g-1) as compared to the control seeds (3000 ng·g-1).

Discussion

Designed synthetic peptides are effective against in controlling a broad spectrum of plant pathogens [5, 7, 9, 19, 36] including difficult-to-control, mycotoxin producing fungal species such as *Aspergillus* and *Fusarium*. Their advantages over naturally occurring peptides include increased resistance to proteolytic degradation [16, 37, 38], no or minimal effect on off-target beneficial microbial populations [22, 23] and they can be integrated into genomes of cultivated field, fruit and ornamental crops [20, 39-41] to provide resistance to diseases and toxin-producing fungal species. In the current study the synthetic antimicrobial peptide AGM182 was designed based on the naturally occurring AMP tachyplesin1 (FIG. 1). Physicochemical properties of AMPs play a significant role on the antimicrobial activity of AMPs. These include net positive charge/charge density, hydrophobicity and others [36]. Though the peptide length and net positive charge in the AGM182 did not differ much with tachyplesin1, hydrophobicity was significantly increased in AGM182 (FIG. 1). Hydrophobicity is one of the important criteria for antimicrobial property of AMPs as it increases the interaction between AMPs and cell membrane of target pathogens. Higher hydrophobicity in AMPs has been shown to increase antimicrobial activity [36]. While designing AGM182, a similar 'central bubble' though preserved in the AGM182 (CLGKFC)(SEQ ID NO: 5) vs. tachyplesin1 (CYRGIC)(SEQ ID NO: 6), the second disulfide linkage was eliminated in AGM182 and replaced by amino acid residues that resulted in amphipathic β-sheet conformation with higher positive charge density (FIG. 1). This positive attribute in dAMP peptides is shown to affect stability and anti-fungal activity [19, 42]. As such, a five-fold higher antimicrobial activity of AGM182 was observed as compared to tachyplesin1 ($IC_{50}$=2.5 μM vs 12.5 μM) in vitro (FIG. 4) and it is attributable to the structural alteration described above. We have also demonstrated the absence of hemolytic activity by this peptide as well. Among different physicochemical properties that positively affect hemolytic activity of AMPs, presence of specific amino acid residues especially tryptophan, has been demonstrated to increase significantly lysis of mammalian erythrocytes by binding to cholesterol present in biological membranes through the indole moiety [43]. Even exclusion of only tryptophan residue in melittin (an AMP from honeybee venom) significantly reduced its hemolytic activity [44]. The absence of tryptophan residue in AGM182 AMP could possibly explain its inability to lyse porcine erythrocytes.

The primary mode of action of these AMPs is membrane damage although AMPs have also been shown to be involved in cellular signaling and can modulate host defense responses [45, 46].

Besides naturally occurring AMPs in plants, synthetic AMPs have demonstrated the ability to restrict pathogen growth in vitro or in planta (through transgenic approaches) [20, 39, 40, 47]. Earlier studies from our lab in cotton showed transgenic expression of a synthetic AMP, D4E1, significantly reduced *A. flavus* growth and aflatoxin production in cottonseed [20]. In this report we have demonstrated, prevention of preharvest aflatoxin contamination in a major food crop such as maize through transgenic expression of a tachyplesin-derived synthetic peptide, AGM182.

Figure 7B:
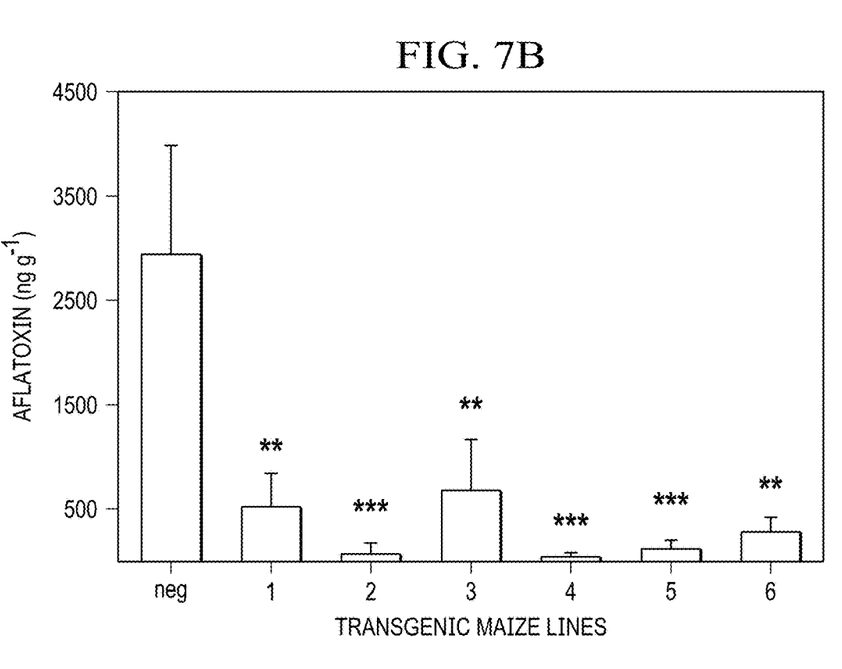

In general, small peptides such as AGM182 used in the current study, could not be detected using the standard Western blotting technique in the transgenic plants. Detection of such small antimicrobial peptides in plants are often challenging due to their small size (18 amino acids in AGM182, FIGS. 1 and 2) and lack of antigenicity to successfully raise antibodies and this observation is in accordance with earlier reports on synthetic peptides [18, 20, 24, 48, 49]. This also could be due to low concentration of the synthetic AGM182 peptide in transgenic maize kernels resulting from possible proteolytic degradation in the plants [16]; yet, the low AGM182 concentration in planta might still be good enough to reduce *A. flavus* growth and subsequent aflatoxin production. A direct correlation between in planta AGM182 production and fungal load in the transgenic maize kernels could not be obtained due to the above-mentioned reasons; however, at the transcript level fungal load correlated well with the expression of AGM182 (FIG. 4, FIGS. 5A-5B, FIG. 7A) in the transgenic kernels and corresponding decrease in aflatoxins (FIG. 7B).

The significant reduction in GFP fluorescence in the seeds of AGM182 transgenic maize lines (FIG. 6) correlated with the reduction in fungal growth (FIG. 7A) and showed that AGM182 is functionally active in the transgenic plants. Aflatoxin levels were drastically reduced (>95%) in the infected AGM182 transgenic seeds (FIG. 7B), which is possibly due to the reduction in fungal load and associated reduction in fungal pathogenicity during seed infection. Similar results were also observed in transgenic cotton seeds expressing the synthetic AMP, D4E1 [20] where, a significant reduction in *A. flavus* growth (45-70%) and aflatoxin production (75-98%) were observed, though the reduction in aflatoxin in the AGM182 transgenic maize seeds are relatively higher than in the D4E1 transgenic cotton seeds. The higher reduction in aflatoxin contamination in maize by AGM182 (vs. D4E1 in cotton) could be due to higher efficacy of AGM182 against *A. flavus* or could be a crop specific response. At this stage, we do not know what other cellular impact AGM182 might have on other metabolic processes in this fungus. In vitro on AGM182-*A. flavus* interaction using RNA-seq [50] in future might reveal the impact of AGM182 on other metabolic processes in the fungus in addition to the known mode of action of AGM182 and other synthetic peptides through destabilization of the fungal cell membrane leading to lysis [7, 19]. Any possible alteration in other metabolic pathways in *A. flavus* by AGM182 could possibly be an indirect effect resulting from the instability of cellular structures caused by the AMP. Transgenic expression of AGM182 in maize on the other hand, did not have any negative effect on plant phenotype and seed weight in the transgenic plants as compared to the control suggesting that AGM182 does not interfere with plant growth and associated yield attributes.

Overall, the results presented here demonstrated the effectiveness of the tachyplesin-derived synthetic peptide AGM182 on controlling *A. flavus* growth and aflatoxin contamination in transgenic maize kernels. In addition, this study highlights the potential application of synthetic biology to design efficiently a safe, synthetic AMP like AGM182. The KSA results, as reported in this study (FIGS. 6 and 7A-7B), have been shown to be directly related to results obtained from field evaluations of corn genotypes [51]. It should be noted that even the best performing transgenic maize lines in this screening recorded aflatoxin levels 60-150 ngg-1 under the optimal conditions. A single, highly contaminated kernel can produce a high aflatoxin value for the entire seed batch. Food and feed safety standards set forth by the European Union, the USA and other countries limit total aflatoxin levels to 4-20 ng·g-1[52]. It is noteworthy that the experimental conditions employed for the kernel screening assay were highly conducive for successful colonization and toxin production by the fungus, which might not be the case under field environments. However, it appears that no single technology can completely inhibit *A. flavus* infection and reduce aflatoxin contamination to allowable levels imposed by regulations set for food and feed commodities [53]. Thus, a combination of technologies such as use of resistant lines bred through classical or molecular approaches [51, 54-57], application of atoxigenic strains to replace toxin-producing strains [58], and good agronomic practices combined with pest control [4, 59] should assist in safeguarding human and livestock from dangerous levels of aflatoxins in contaminated food and feed. Conspicuously, much of the adverse health impacts due to aflatoxin-contaminated food and feed crops in developing countries results from consumption of improperly stored produce; hence, it is essential to explore avenues for control of aflatoxin contamination during storage and handling as well.

REFERENCES

[1] CAST, Aflatoxins and other mycotoxins: An agricultural perspective, in, Council for Agricultural and Science Technology Reports, 2003.

[2] F. Wu, Mycotoxin reduction in Bt corn: potential economic, health, and regulatory impacts, Transgenic Res., 15 (2006) 277-289.

[3] N. Mitchell, E. Bowers, C. Hurburgh, F. Wu, Potential economic losses to the USA corn industry from aflatoxin contamination, Food Additives & Contaminants: Part A, 33 (2016) 540-550.

[4] P. Udomkun, A. N. Wiredu, M. Nagle, J. Müller, B. Vanlauwe, R. Bandyopadhyay, Innovative technologies to manage aflatoxins in foods and feeds and the profitability of application—A review, Food Control, 76 (2017) 127-138.

[5] J. F. Marcos, A. Munoz, E. Perez-Paya, S. Misra, B. Lopez-Garcia, Identification and rational design of novel antimicrobial peptides for plant protection, Annu. Rev. Phytopathol., 46 (2008) 273-301.

[6] K. Rajasekaran, A. J. De Lucca, J. W. Cary, Aflatoxin control through transgenic approaches, Toxin Rev., 28 (2009) 89-101.

[7] K. Rajasekaran, J. W. Cary, C. A. Chlan, Jaynes J. M., B. D., Strategies for controlling plant diseases and mycotoxin contamination using antimicrobial synthetic peptides, in: K. Rajasekaran, J. W. Cary, J. M. Jaynes, E. Montesinos (Eds.) ACS Symposium Book Series #1095: Small Wonders: Peptides for Disease Control, 2012, pp. 295-315.

[8] E. Montesinos, Antimicrobial peptides and plant disease control, FEMS Microbiol. Lett., 270 (2007) 1-11.

[9] J. W. Cary, K. Rajasekaran, R. L. Brown, M. Luo, Z. Y. Chen, D. Bhatnagar, Developing resistance to aflatoxin in maize and cottonseed, Toxins (Basel), 3 (2011) 678-696.

[10] M. Zasloff, Antimicrobial peptides of multicellular organisms, Nature, 415 (2002) 389-395.

[11] R. E. W. Hancock, H. G. Sahl, Antimicrobial and host-defense peptides as new anti-infective therapeutic strategies, Nat. Biotechnol., 24 (2006) 1551-1557.

[12] T. Ganz, Defensins: antimicrobial peptides of innate immunity, Nat Rev Immune, 3 (2003) 710-720.

[13] S. C. Barr, D. Rose, J. M. Jaynes, Activity of lytic peptides against intracellular *Trypanosoma cruzi* amastigotes in vitro and parasitemias in mice, J. Parasitol., 81 (1995) 974-978.

[14] I. A. Edwards, A. G. Elliott, A. M. Kavanagh, J. Zuegg, M. A. Blaskovich, M. A. Cooper, Contribution of amphipathicity and hydrophobicity to the antimicrobial activity and cytotoxicity of beta-hairpin peptides, ACS Infect Dis, 2 (2016) 442-450.

[15] U. Schwab, P. Gilligan, J. M. Jaynes, D. Henke, In vitro activities of designed antimicrobial peptides against multidrug-resistant cystic fibrosis pathogens, Antimicrob. Agents Chemother., 43 (1999) 1435-1440.

A. J. DeLucca, J. M. Bland, C. Grimm, T. J. Jacks, J. W. Cary, J. M. Jaynes, T. E. Cleveland, T. J. Walsh, Fungicidal properties, sterol binding, and proteolytic resistance of the synthetic peptide D4E1, Canadian Journal of Microbiology, 44 (1998) 514-520.

[16] M. R. Yeaman, N.Y. Yount, Mechanisms of antimicrobial peptide action and resistance, Pharmacol. Rev., 55 (2003) 27-55.

[17] J. W. Cary, K. Rajasekaran, J. M. Jaynes, T. E. Cleveland, Transgenic expression of a gene encoding a synthetic antimicrobial peptide results in inhibition of fungal growth in vitro and in planta, Plant Sci., 154 (2000) 171-181.

[18] K. Rajasekaran, K. D. Stromberg, J. W. Cary, T. E. Cleveland, Broad-spectrum antimicrobial activity in vitro of the synthetic peptide D4E1, J. Agric. Food Chem., 49 (2001) 2799-2803.

[19] K. Rajasekaran, J. W. Cary, J. M. Jaynes, T. E. Cleveland, Disease resistance conferred by the expression of a gene encoding a synthetic peptide in transgenic cotton (*Gossypium hirsutum* L.) plants, Plant Biotechnol. J., 3 (2005) 545-554.

[20] K. Rajasekaran, J. W. Cary, J. J. M., E. Montesinos, Small Wonders: Peptides for Disease Control, American Chemical Society Symposium Series 1095, Washington, D C, 2012.

[21] J. M. Stewart, C. A. Nader, K. Rajasekaran, Effect of antimicrobial peptides (AMPs) on mycorrhizal associations, AAES Research Series, 562 (2007) 163-166.

[22] M. O'Callaghan, E. M. Gerard, N. W. Waipara, S. D. Young, T. R. Glare, P. J. Barrell, A. J. Conner, Microbial communities of *Solanum tuberosum* and magainin-producing transgenic lines, Plant Soil, 266 (2004) 47-56.

[23] M. Schubert, M. Houdelet, K. H. Kogel, R. Fischer, S. Schillberg, G. Nolke, Thanatin confers partial resistance against aflatoxigenic fungi in maize (*Zea mays*), Transgenic Res., 24 (2015) 885-895.

[24] Z. Y. Chen, K. Rajasekaran, R. L. Brown, R. J. Sayler, D. Bhatnagar, Discovery and confirmation of genes/proteins associated with maize aflatoxin resistance, World Mycotoxin Journal, 8 (2015) 211-224.

[25] T. Miyata, F. Tokunaga, T. Yoneya, K. Yoshikawa, S. Iwanaga, M. Niwa, T. Takao, Y. Shimonishi, Antimicrobial Peptides, Isolated from Horseshoe Crab Hemocytes, Tachyplesin II, and Polyphemusins I and II: Chemical Structures and Biological Activity, Journal of Biochemistry, 106 (1989) 663-668.

[26] G. Wang, X. Li, Z. Wang, APD3: the antimicrobial peptide database as a tool for research and education, Nucleic Acids Res., 44 (2016) D1087-1093.

[27] K. McGinnis, V. Chandler, K. Cone, H. Kaeppler, S. Kaeppler, A. Kerschen, C. Pikaard, E. Richards, L. Sidorenko, T. Smith, N. Springer, T. Wulan, Transgene induced RNA interference as a tool for plant functional genomics, Methods Enzymol., 392 (2005) 1-24.

[28] J. C. Rogers, Two barley alpha-amylase gene families are regulated differently in aleurone cells, J. Biol. Chem., 260 (1985) 3731-3738.

[29] B. Frame, M. Main, R. Schick, K. Wang, Genetic transformation using maize immature zygotic embryos, in: Methods Mol Biol, Springer Science+Business Media, LLC, Clifton, N.J., 2011, pp. 327-341.

[30] K. Rajasekaran, R. Majumdar, C. Sickler, Q. Wei, J. Cary, D. Bhatnagar, Fidelity of a simple Liberty leaf-painting assay to validate transgenic maize plants expressing the selectable marker gene, bar, Journal of Crop Improvement, 31 (2017) 628-636.

[31] K. Rajasekaran, C. M. Sickler, R. L. Brown, J. W. Cary, D. Bhatnagar, Evaluation of resistance to aflatoxin contamination in kernels of maize genotypes using a GFP-expressing *Aspergillus flavus* strain World Mycotoxin Journal, 6 (2013) 151-158.

[32] X. Shu, D. P. Livingston, R. G. Franks, R. S. Boston, C. P. Woloshuk, G. A. Payne, Tissue-specific gene expression in maize seeds during colonization by *Aspergillus flavus* and *Fusarium verticillioides*, Mol. Plant Pathol., 16 (2015) 662-674.

[33] K. Rajasekaran, J. W. Cary, P. J. Cotty, T. E. Cleveland, Development of a GFP-expressing *Aspergillus flavus* strain to study fungal invasion, colonization, and resistance in cottonseed, Mycopathologia, 165 (2008) 89-97.

[34] R. L. Brown, P. J. Cotty, T. E. Cleveland, N. W. Widstrom, Living maize embryo influences accumulation of aflatoxin in maize kernels, J Food Protect, 56 (1993) 967-971.

[35] K. Rajasekaran, J. M. Jaynes, J. W. Cary, Transgenic expression of lytic peptides in food and feed crops to control phytopathogens and preharvest mycotoxin contamination, in:

M. Appell, Kendra, D. F., Trucksess, M. W. (Ed.) Mycotoxin Prevention and Control in Agriculture, American Chemical Society, 2009, pp. 119-142.

[36] L. D. Owens, T. M. Heutte, A single amino acid substitution in the antimicrobial defense protein cecropin b is associated with diminished degradation by leaf intercellular fluid, Mol. Plant-Microbe Interact., 10 (1997) 525-528.

[37] Q. Liu, J. Ingersoll, L. Owens, S. Salih, R. Meng, F. Hammerschlag, Response of transgenic Royal Gala apple (*Malus×domestica* Borkh.) shoots carrying a modified cecropin MB39 gene, to *Erwinia amylovora*, Plant Cell Rep., 20 (2001) 306-312.

[38] A. Chakrabarti, T. R. Ganapathi, P. K. Mukherjee, V. A. Bapat, MSI-99, a magainin analogue, imparts enhanced disease resistance in transgenic tobacco and banana, Planta, 216 (2003) 587-596.

[39] K. Kamo, D. Lakshman, G. Bauchan, K. Rajasekaran, J. Cary, J. Jaynes, Expression of a synthetic antimicrobial peptide, D4E1, in *Gladiolus* plants for resistance to *Fusarium oxysporum* f. sp. *gladioli*, Plant Cell Tiss Organ Cult, 121 (2015) 459-467.

[40] L. C. Mejia, M. J. Guiltinan, Z. Shi, L. Landherr, S. N. Maximova, Expression of designed antimicrobial peptides in *Theobroma cacao* L. trees reduces leaf necrosis caused by *Phytophthora* spp., in: K. Rajasekaran, J. W. Cary, J. Jaynes, M., E. Montesinos (Eds.) Small Wonders: Peptides for Disease Control, American Chemical Society, Washington, D.C., 2012, pp. 379-395.

[41] J. M. Jaynes, G. C. Bernard, Structure/Function Link Between Cytokine Domains and Natural and Designed Lytic Peptides: Medical Promise, in: K. Rajasekaran, J. W. Cary, J. M. Jaynes, E. Montesinos (Eds.) Small Wonders: Peptides for Disease Control, American Chemical Society, Washington, D.C., 2012, pp. 21-45.

[42] B. Dekruijff, Cholesterol as target for toxins, Biosci Rep, 10 (1990) 127-130.

[43] S. E. Blondelle, R. A. Houghten, Hemolytic and antimicrobial activities of the twenty-four individual omission analogues of melittin, Biochemistry, 30 (1991) 4671-4678.

[44] J. D. F. Hale, R. E. W. Hancock, Alternative mechanisms of action of cationic antimicrobial peptides on bacteria, Expert Review of Anti-infective Therapy, 5 (2007) 951-959.

[45] M. Rahnamaeian, Antimicrobial peptides, Plant Signaling & Behavior, 6 (2014) 1325-1332.

[46] R. Mentag, M. Luckevich, M. J. Morency, A. Seguin, Bacterial disease resistance of transgenic hybrid poplar expressing the synthetic antimicrobial peptide D4E1, Tree Physiology, 23 (2003) 405-411.

[47] G. DeGray, K. Rajasekaran, F. Smith, J. Sanford, H. Daniell, Expression of an antimicrobial peptide via the chloroplast genome to control phytopathogenic bacteria and fungi, Plant Physiol., 127 (2001) 852-862.

[48] A. Koch, W. Khalifa, G. Langen, A. Vilcinskas, K.-H. Kogel, J. Imani, The antimicrobial peptide thanatin reduces fungal infections in *Arabidopsis*, J. Phytopathol., 160 (2012) 606-610.

[49] R. Bedre, K. Rajasekaran, V. R. Mangu, L. E. Sanchez Timm, D. Bhatnagar, N. Baisakh, Genome-wide transcriptome analysis of cotton *Gossypium hirsutum* L.) identifies candidate gene signatures in response to aflatoxin producing fungus *Aspergillus flavus*, PLoS ONE, 10 (2015) e0138025.

[50] W. P. Williams, M. D. Krakowsky, B. T. Scully, R. L. Brown, A. Menkir, M. L. Warburton, G. L. Windham, Identifying and developing maize germplasm with resistance to accumulation of aflatoxins, World Mycotoxin Journal, 8 (2015) 193-209.

[51] Anonymous, The Value of Proactive Mycotoxin Prevention in the Age of the Food Safety Modernization Act—a White Paper, in, Vicam, Waters Corporation, 2017, pp. 8.

[52] J. Gressel, G. Polturak, Suppressing aflatoxin biosynthesis is not a breakthrough if not useful—a perspective, Pest Manage. Sci., 74 (2018) 17-21.

[53] J. O. Masanga, J. M. Matheka, R. A. Omer, S. C. Ommeh, E. O. Monda, A. E. Alakonya, Downregulation of transcription factor aflR in *Aspergillus flavus* confers reduction to aflatoxin accumulation in transgenic maize with alteration of host plant architecture, Plant Cell Rep., 34 (2015) 1379-1387.

[54] R. Majumdar, K. Rajasekaran, J. W. Cary, RNA Interference (RNAi) as a potential tool for control of mycotoxin contamination in crop plants: Concepts and considerations, Frontiers in Plant Science, 8 (2017).

[55] D. Thakare, J. Zhang, R. A. Wing, P. J. Cotty, M. A. Schmidt, Aflatoxin-free transgenic maize using host-induced gene silencing, Science Advances, 3 (2017) 1-8.

[56] P. Bhatnagar-Mathur, S. Sunkara, M. Bhatnagar-Panwar, F. Waliyar, K. K. Sharma, Biotechnological advances for combating *Aspergillus flavus* and aflatoxin contamination in crops, Plant Sci., 234 (2015) 119-132.

[57] P. J. Cotty, Method for the control or prevention of aflatoxin contamination using a non-toxigenic strain of *Aspergillus flavus*, in: U.S. Pat. No. 5,294,442, USA, 1994.

[58] G. P. Munkvold, Cultural and genetic approaches to managing mycotoxins in maize, Annu. Rev. Phytopathol., 41 (2003) 99-116.

What is claimed is:

1. A method to produce transgenic maize lines expressing a synthetic AGM182 peptide, the method comprising the steps of:
   producing a transgenic maize line through an *agrobacterium* mediated transformation of the AGM182 gene into immature maize embryos, wherein the AGM182 gene comprises a 129 bp nucleic acid of SEQ ID NO:3.

2. The method as claimed in claim 1, wherein the nucleic acid of SEQ ID NO:3 encodes an amino acid sequence of the AGM182 peptide of SEQ ID NO: 4.

3. The method as claimed in claim 1, wherein the AGM182 peptide is effective against mycotoxin producing fungal species and with no toxicity against mammals.

4. The method as claimed in claim 1, wherein the AGM182 peptide reduces the growth of the mycotoxin producing fungal species *Aspergillus Flavus.*

5. The method as claimed in claim 1, wherein the AGM182 peptide reduces the growth of *Aspergillus Flavus* by 72% in transgenic maize lines.

6. The method as claimed in claim 1, wherein the AGM182 peptide reduces the growth of mycotoxin producing fungal species, wherein the fungal species is *Fusarium.*

7. The method as claimed in claim 3, wherein the mycotoxin is aflatoxin.

8. The method as claimed in claim 1, wherein the AGM182 peptide reduces an aflatoxin contamination by 76-98% in transgenic maize lines.

9. A transgenic maize line expressing an AGM182 peptide of SEQ ID NO:4 that reduces aflatoxin production and fungal growth of *Aspergillus Flavus.*

10. The transgenic maize line as claimed in claim 9, wherein the synthetic AGM182 peptide, reduces the growth of the *Aspergillus Flavus* by 72%.

11. The transgenic maize line as claimed in claim 9, wherein the synthetic AGM182 peptide reduces the aflatoxin contamination by 76-98%.

12. An antimicrobial peptide AGM182 of SEQ ID NO:4.

13. The antimicrobial peptide as claimed in claim 12, wherein the synthetic antimicrobial AGM182 peptide has a five-fold higher antimicrobial activity (IC50=2.5 μM) compared to naturally occurring antimicrobial peptide tachyplesin 1 (IC50=12.5 μM).

14. A vector comprising an AGM182 gene that comprises a 129 bp nucleic acid of SEQ ID NO:3.

15. The vector of claim 14, wherein the vector is an expression vector.

16. The vector of claim 14, wherein the vector is a pMCG 1005 plasmid and the AGM182 gene is operatively linked to a constitutive Ubi-1 (maize) promoter.

17. The vector of claim 14, wherein the vector further comprises a maize alcohol dehydrogenase-1 (Adh-1) intron that is 5' from the AGM182 gene start codon, wherein the Adh-1 intron improves the expression of the AGM182 gene.

18. The vector of claim 14, wherein the vector further comprises a barley alpha amylase signal peptide (BAAS) nucleic acid sequence that is 5' from the AGM182 gene, wherein the BAAS peptide increases the efficiency of the synthetic AGM182 peptide excretion from the host cell to the cell wall.

19. A method of preventing or treating a plant to reduce a growth of a mycotoxin producing fungal species comprising:
    spraying a seed, seedling, or plant with an AGM182 peptide of SEQ ID NO: 4 in an amount sufficient to prevent or treat the growth of the mycotoxin producing fungal species.

\* \* \* \* \*